US006492576B2

(12) United States Patent
Kihara et al.

(10) Patent No.: US 6,492,576 B2
(45) Date of Patent: Dec. 10, 2002

(54) METHOD FOR IDENTIFYING A BARLEY VARIETY AND A BARLEY HAVING A BREWING PROPERTY

(75) Inventors: Makoto Kihara, Gunma-ken (JP); Takafumi Kaneko, Gunma-ken (JP); Kensuke Fukuda, Gunma-ken (JP); Kazutoshi Ito, Gunma-ken (JP)

(73) Assignee: Sapporo Breweries Ltd., Tokyo (JP)

( * ) Notice: Subject to any disclaimer, the term of this patent is extended or adjusted under 35 U.S.C. 154(b) by 0 days.

(21) Appl. No.: 09/104,536

(22) Filed: Jun. 26, 1998

(65) Prior Publication Data

US 2002/0019994 A1 Feb. 14, 2002

(30) Foreign Application Priority Data

Jun. 26, 1997 (JP) .............................. 9-170582

(51) Int. Cl.⁷ .............................. A01H 5/00; A01H 1/00
(52) U.S. Cl. ....................... 800/260; 800/266; 800/267; 800/320
(58) Field of Search ................................ 800/298, 320, 800/260, 266, 267

(56) References Cited

U.S. PATENT DOCUMENTS 5,807,676 A * 9/1998 Tsuchiya et al. ................ 435/6

FOREIGN PATENT DOCUMENTS

| EP | 0 454 232 | 10/1991 |
| EP | 0 704 540 | 4/1996 |
| EP | 0 713 916 | 5/1996 |
| WO | WO 95/35026 | 12/1995 |
| WO | WO 97/02353 | 1/1997 |

OTHER PUBLICATIONS

LaBerge et al. Journal of the American Society of Brewing Chemists. vol. 45, No. 4, pp. 140–145, 1987.*
Lin et al. Acta Genetica Sinica. vol. 19, pp. 122–130, 1992.*
Yoshigi et al. Journal of Biochemistry. vol. 115, pp. 47–51, 1994.*
Allison et al. 58th Annual Report, SPBS, Edinburgh, pp. 92–139, 1979.*
LaBerge et al. Journal of the American Society of Brewing Chemists. vol. 45, pp. 140–145, 1987.*
Lin et al. Acta Genetica Sinica. vol. 19, pp. 122–130 (translation 1–20), 1992.*
Yoshigi et al. Journal of Biochemistry. vol. 115, pp. 47–51, 1994.*
Allison et al. Breeding for malting quality at the Scottish Plant Breeding Station. 58th Annual Report, SPBS, Edinburgh. pp. 92–139, 1979.*
Eglinton et al. Preliminary characterisation of two forms of barley beta–amylase. V IOC & VII IBGS, poster #3 pp. 8–10, 1996.*

LaBerge et al. Changes in beta–amylase enzymes of barley during malting. Journal of the American Society of Brewing Chemists. vol. 45, pp. 140–145, 1987.*
Lin et al. Studies of beta–amylase isozyme in mature grains of two–rowed barley and its hybrids. Acta Genetica Sinica. vol. 19, pp. 12–130, 1992.*
Yoshigi et al. PCR Cloning and sequencing of the beta–amylase cDNA from barley. Journal of Biochemistry. vol. 115, pp. 47–51, 1994.*
S. Weining, et al., Theoretical and Applied Genetics, vol. 82, No. 2, pp. 209–216, "Identification and Mapping of Polymorphisms in Cereals Based on the Polymerase Chain Reaction", 1991.
P. W. Chee, et al., Journal of the American Society of Brewing Chemists, vol. 51, No. 3, pp. 93–96, "Development of Polymerase Chain Reaction for Barley Genome Analysis", 1993.
Robert Lundgard, et al., Carlsberg Research Communications, vol. 51, No. 7, pp. 487–491, "Limited Proteolysis in the Carboxy–Terminal Region of Barley Beta–Amylase", 1986.
J. Hejgaard, Journal of the Institute of Brewing, vol. 84, pp. 43–46, "'Free' and 'bound' Beta–Amylases During Malting of Barley. Characterization by Two–Dimensional Immunolectrophoresis", 1978.
I. O. Foda, et al., Egyptian Journal of Microbiology, vol. 10, No. 1–2, pp. 45–56, "Enzymic Studies on Egyptian Malt 11. Effect of Temperature on Amino Acids Content and Amylase Activity During and After Brewing", 1975.
D. Von Wettstein, International Atomic Energy Agency, pp. 67–76, "Breeding of Value Added Barley by Mutation and Protein Engineering", 1995.
D. E. Briggs, et al., Journal of Cereal Science, vol. 3, No. 1, pp. 67–72, "Alpha–Amylase Isoenzymes of Germinated Barley", 1985.
Youichi Tsuchiya et al., "Identification of Malting Barley Varieties by Genome Analysis", EBC Congress, 1995, p109–p116.
J.K. Eglinton et al, "Preliminary Characterisation of Two Forms of Barley Beta–Amylase", V IOC & VII IBGS, 1996, poster #3 p8–p10.

* cited by examiner

*Primary Examiner*—Elizabeth F. McElwain
(74) *Attorney, Agent, or Firm*—Oblon, Spivak, McClelland, Maier & Neustadt, P.C.

(57) ABSTRACT

A method for identifying barley with good brewing properties using the thermostability of the barley β-amylase as an indicator. The thermostability of the barley β-amylase significantly affects the degree of the apparent attenuation limit. A method for determining the enzyme activity of a extract solution from one barley seed, an indirect method by an isoelectric point, and an indirect identifying method by DNA polymorphisms of the region containing the β-amylase structural gene have been developed as a method for determining the type of thermostability for a barley β-amylase. The selection method is not affected by environmental or climatic conditions.

9 Claims, 2 Drawing Sheets

X: Relation between the relative remaining activity of β-amylase and Apparent Attenuation Limit (AAL)

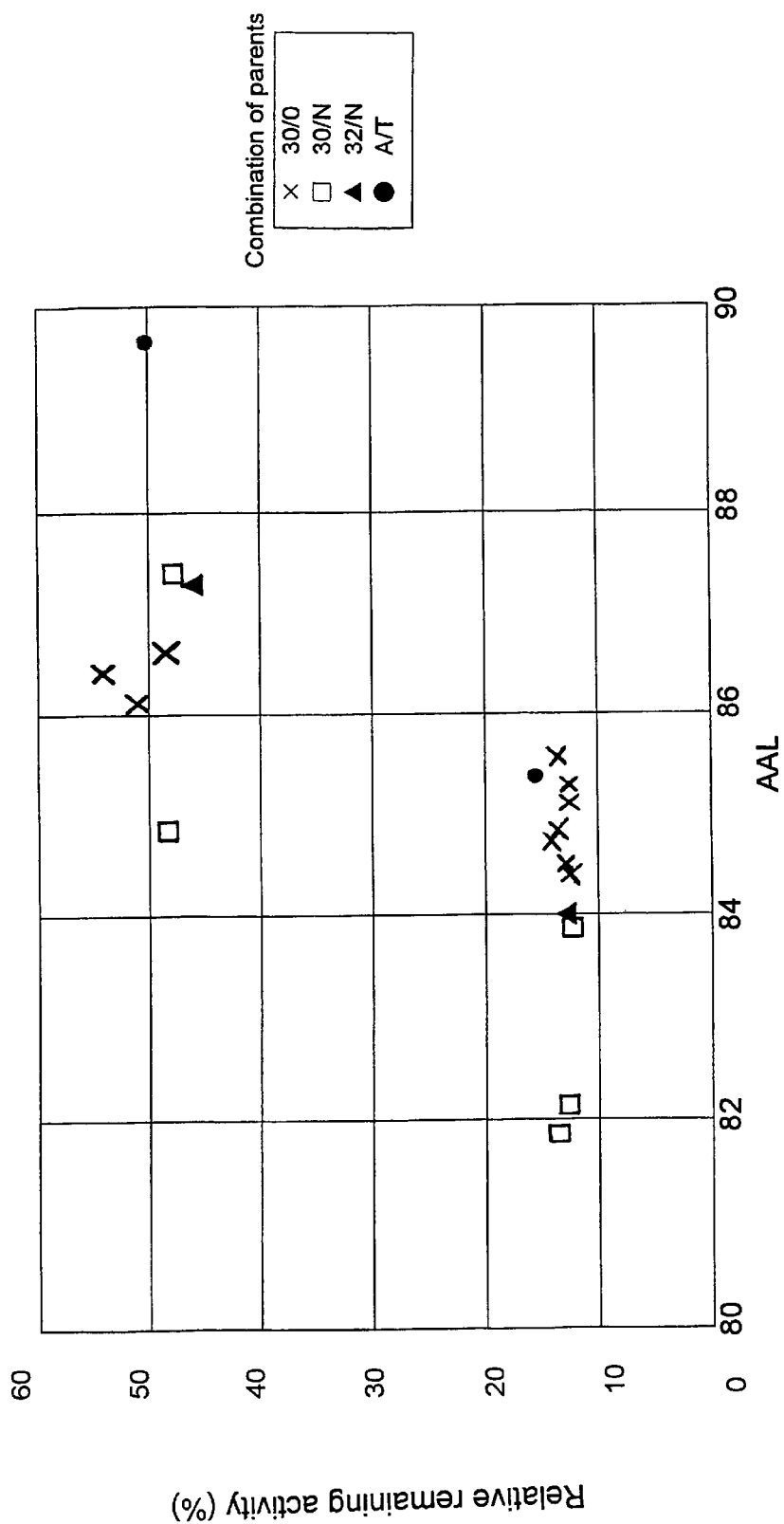

METHOD FOR IDENTIFYING A BARLEY VARIETY AND A BARLEY HAVING A BREWING PROPERTY

BACKGROUND OF THE INVENTION

1. Field of the Invention

The invention relates to a method for identifying a barley variety using the thermostability of β-amylase encoded by the barley as an indicator. The invention also relates to a method for identifying a barley for brewing using this thermostability of the β-amylase as an indicator. Furthermore, the invention relates to a method of breeding method of a barley variety and a barley variety bred according to this breeding method, using the barley variety identified by the method of the present invention.

2. Description of the Background Art

Malting barley is conventionally bred using a traditional mating technique, for the most part comprising the following two steps. In the first step, individuals having different genotype are mated together and subsequently a selection is conducted from many resultant progeny lines based on desirable cultivation properties such as agricultural properties, adaptability to an environment, and resistance to disease, and a selected line is genetically fixed by growing. This step takes in the neighborhood of 5–6 years. After this long first step, in the second step, a malt analysis of many lines selected and grown in the first step is made, and only good barley lines are selected according to the result of the analysis of their brewing property. The selected barley lines are bred for malting barley.

In conventional barley breeding, however, survey and selection of brewing properties cannot be conducted during the first step. Therefore, a selection and breeding of agronomic character must be performed from grand scale mated progeny lines and then followed by genetic fixation. Moreover, the existence of a good barley line with favorable brewing properties is not guaranteed.

The breeding of a desirable line using this method largely depends on whether an individual breeder can identify a barley having a good brewing property using his experience and observations. Therefore, the breeding of a malting barley having the desired brewing properties must rely on the experience of a brilliant breeder.

Furthermore, the brewing property used as an indicator for selecting a good line in the conventional method largely depends on environmental and climatic conditions. Therefore, the evaluation of characteristics associated with brewing properties must be conducted over the course of several years.

As described above, the conventional method for breeding malting barley with improved brewing properties requires an experienced and skilled barley breeder. Further, even a highly skilled barley breeder requires a long breeding time and tremendous effort to identify malting barley having good brewing properties.

On the other hand, in the past, studies on biochemical differences of β-amylase among barley varieties have been conducted, based on the knowledge that β-amylase is a very important enzyme as a carbohydrase in the brewing of beer. These studies have indicated that there are differences in a gene region coding for β-amylase among barley varieties (Tsuchiya et al. 1995, proceedings of EBC, 109–116). Further, it has been reported that barley varieties can be classified into two types by the isoelectric focusing pattern of β- amylase (Eglinton et al. 1996, Proceedings of V IOC & VII IBGS, 8–10).

However, no relationship between the biological/biochemical properties of β-amylase and the beer brewing property among barley varieties has been found.

SUMMARY OF THE INVENTION

As a result of considerable research effort, the inventors have found that there is a relationship between the biological property of β-amylase and the beer brewing property among barley varieties. Using these findings, they have developed a method for identifying varieties that is not affected by natural environment such as climate and the brewing property can be evaluated early after the initiation of breeding.

As described above, the inventors have made numerous research efforts toward the method for identifying a character of interest, by which the breeding period and amount of labor in the breeding of barley is reduced. As a result of this, they have found that there are differences in the degree of a thermostability of β-amylase enzyme activity among barley varieties, and that these differences in thermostability significantly influence the beer brewing property. Further, the research has revealed that the varieties can be identified by differences in thermostability of β-amylase among barley varieties. According to these findings, the inventors have discovered a method for identifying and breeding barley varieties having a good brewing property, or suitability for brewing, using the thermostability of β-amylase as an indicator.

Therefore, the inventive method for identifying barley varieties is characterized by identifying barley varieties, based on the thermostability of β-amylase which the barley varieties encode. Therefore, barley varieties have different thermostability of β-amylase respectively, and it is possible to identify varieties conveniently, based on this thermostability.

The term "thermostability" as described herein may be expressed as the term "heat resistance" which is used to indicate the remaining enzyme activity after heating. Specifically, the thermostability of β-amylase can be expressed, based on the remaining enzyme activity after the heat treatment of, for example 57.5° C. for 30 minutes. The treatment conditions are not limited to this temperature and time only but includes any temperature and heating time. Therefore, all such methods are included in the present invention, wherein the thermostability is determined by the remaining enzyme activity after heating and the varieties are identified, based on this thermostability.

Also, as described above, the inventors have discovered that the thermostability of β- amylase significantly influences the brewing property, and have developed a method for identifying a more suitable barley variety for brewing. Therefore, the inventive method for identifying a barley variety allows the selection of a barley variety having a good brewing property by selecting a variety with a greater thermostability of β-amylase.

For example, a suitable variety for brewing is a barley which retains 20% or more, preferably 30% or more, more preferably 40% or more, of the activity of non-heated β-amylase after heating sample such as an extract solution of barley at the above 57.5° C. for 30 minutes. This temperature, however, is illustrative only, and the thermostability also can be determined at other than this temperature, and the determination of the thermostability by different temperature and treatment time is included in the present invention.

As described above, unlike the conventional method depending on the experience of a breeder, the present invention makes it possible to objectively identify a variety with a preferable brewing property, based on a physical property of the thermostability of β-amylase of a barley in breeding. This makes it possible to simply and certainly select a barley variety with a preferable brewing property.

Further, the inventors have found that there is a correlation between the thermostability of β-amylase and the isoelectric point value of β-amylase and have also found that the gene coding for β-amylase (the β-amylase gene) has polymorphisms among varieties and that there is a correlation between these polymorphisms and β-amylase. Therefore, these findings allow indirect measurement based on isoelectric points or gene sequences rather than direct measurement of the thermostability of β-amylase which each barley variety possesses. In recent years, advancements in biotechnology have caused the development and improvement of various analytical apparatus and the like, and, by utilizing these, simple measurement based on the isoelectric points or gene sequences, rather than direct measurement of the thermostability, is possible. This in turn makes it possible to more easily identify and select a barley variety with a good brewing property. Of course, these methods for indirectly measuring the thermostability may be employed alone, while it is possible to more effectively identify a desired variety, by combining these methods.

The determination of the above-described thermostability may be conducted using an enzyme solution or nucleic acid solution collected from each barley variety. More particularly, when determining the thermostability after heating, or when determining the isoelectric point, the enzyme solution collected from seeds or the like of each barley variety can be used. These seeds for obtaining the enzyme solution can be used in any growth stage, but fully ripe seeds are preferably used. Further, when determining polymorphisms of β- amylase, the nucleic acid solution collected from tissues and cells of, for example, green leaves of each barley variety can be utilized. Any growth stage of tissues and cells can be used herein, regardless of their growth stage. Therefore, by obtaining the enzyme solution or nucleic acid solution from an early growth stage of barley, it is possible to dramatically shorten the time required to judge as compared to a conventional method, and it is possible to rapidly identify a variety with a brewing property. This allows not only an advantage with respect to time-saving but also reduces of the cost of examination associated with the conventional method.

Further, a barley variety having the desired thermostability of β-amylase, or a barley variety with a good brewing property or greater suitability for brewing can be bred according to the present invention. As a result of this, it is possible to maintain, improve, or develop the quality of a beer product by utilizing the barley variety bred herein for manufacturing beer.

Moreover, it is possible to provide a better brewed product by using the barley variety having such good brewing property for manufacturing the brewed product.

A more complete appreciation of the present invention and many of the attendant advantages thereof will be readily obtained as the same becomes better understood by reference to the following detailed description when considered in connection with the following drawings.

BRIEF DESCRIPTION OF THE DRAWINGS

FIG. 2 shows the relation between the relative remaining activity and the degree of apparent attenuation limit in the thermostability of β-amylase of progeny lines wherein the same varieties are mated.

DETAILED DESCRIPTION OF THE PREFERRED EMBODIMENTS

Figure 1:
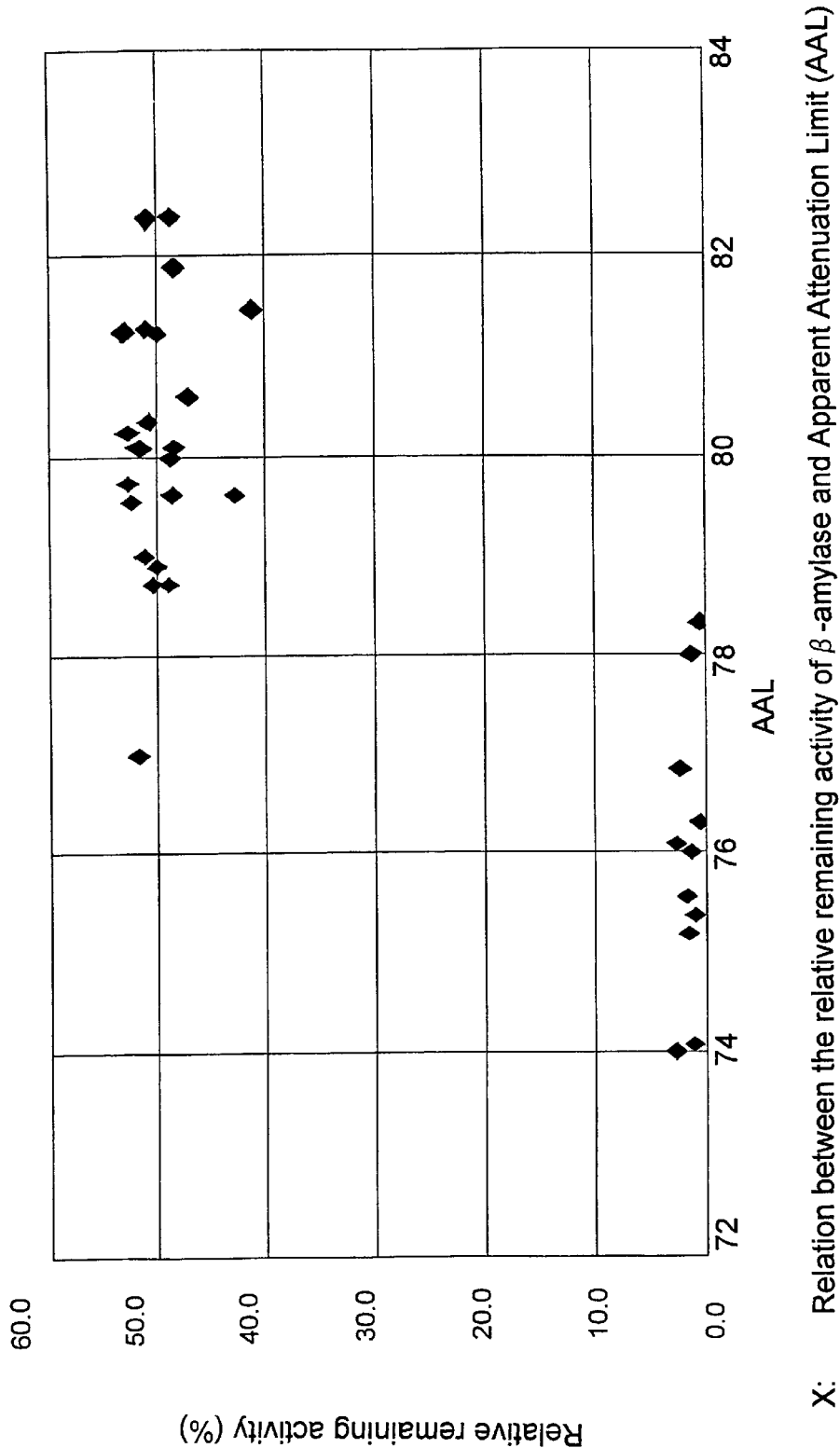
FIG. 1 shows the relationship between the relative remaining activity and the degree of apparent attenuation limit in the thermostability of β-amylase.

The preferred embodiments of the present invention will now be explained in detail.

1. Classification of a Barley Variety Based on the Thermostability of β-amylase

Barley varieties are classified into four groups based on the thermostability of β- amylase by a determination method described below.

The thermostability of β-amylase can be determined by a direct method or an indirect method. One direct method is determining the thermostability from the remaining enzyme activity after heating at constant conditions. Examples of indirect methods include a method based on the isoelectric point of β-amylase and a method based on polymorphisms of the β- amylase gene region. These methods and their features will be explained below.

(1) Determination of Thermostability Based on Enzyme Activity (Direct Method).

A crude enzyme solution is extracted from barley seeds. Fully ripe barley seeds are preferably used. When extracting a crude enzyme solution, a buffer solution which does not inhibit the activity of β-amylase, for example a phosphate buffer solution containing 1 mM of dithiothreitol, is used. After the resultant extract solution is centrifuged, the supernatant is used as a crude enzyme solution. Next, the thermostability of β-amylase is investigated using the crude enzyme solution. The enzyme solution is treated with heat, followed by the determination of the activity of β-amylase. An optimal condition of the heat treatment is around 57.5° C. for around 30 minutes, but the invention is not limited to this temperature condition, and it is possible to determine the thermostability under other conditions. In the determination of the activity of β-amylase, specifically 2,4-dichlorophenyl β-maltopentaoside (Ono Pharmaceutical Co. Ltd.) may be used as a substrate, and is allowed to be reacted with the enzyme at 37° C. One unit of β-amylase activity is defined as the amount of the enzyme required to provide 1 $\mu$mole of 2,4-dichlorophenol per one minute. The relative remaining activity is then calculated by standardizing the values determined with a control of the activity of the enzyme which is not treated with heat.

Barley varieties are classified into 3 groups, and the order of decreasing relative remaining activity determined herein, or decreasing thermostability, is given below (Table 1). These three groups are conveniently referred as type A, B, and C respectively. Type A has 40% or more of the relative remaining activity, and type B has about 10–30% or more. Type C is a variety which loses most enzyme activity by the heat treatment.

Since the relative remaining activity obtained by the above determination method vanes among barley varieties (Table 1), it is possible to identify the thermostability of each variety based on this relative remaining activity.

(2) Determination of the Isoelectric Point of β-amylase.

The crude enzyme solution prepared by the above method is applied to isoelectric focusing electrophoresis, using a support such as starch gel and acrylamide gel. After electrophoresis, the gel is reacted with a substrate of starch and a staining solution of iodine solution to determine the isoelectric point. The method of isoelectric focusing electrophoresis, which is not limited, is conducted by using various methods and kits and the like.

According to the results of the determination of the isoelectric point of β-amylase, the barley varieties are classified into two types by the existence of a band with a pI of 6.5. These two types will be described in detail. One type without a band of pI 6.5 is referred to as Sd1, the other type with a band of pI 6.5 is referred to as Sd2.

(3) Determination of DNA Polymorphisms in the β-amylase Gene Region.

Genomic DNA is extracted from barley tissues. The tissues used in DNA extraction, though not limited, is preferably green leaves. CTAB method (Murray et al. 1980, Nucleic Acids Res. 8:4321–4325, incorporated herein by reference), Ethidium bromide method (Varadarajan and Prakash 1991, Plant Mol. Biol. Rep. 9:6–12, incorporated herein by reference), or a like method is used to extract DNA.

Next, the polymorphisms in the region containing the barley β-amylase gene are examined. For example, in a polymorphism analysis of the structural gene by the RFLP method, genomic DNA extracted from plants is cleaved with restriction enzymes, and subsequently is fractionated by electrophoresis. After fractionation, the polymorphisms are detected by the Southern hybridization method (Southern et al. 1975, J. Mol. Biol. 98: 503–517, incorporated herein by reference). As a probe, for example, a part of the structural gene of β-amylase, the entire promoter region (WO 97/02353, incorporated herein by reference), or a portion thereof, or the like may be used.

The results of this determination are classified into three types of patterns corresponding to the above three types classified by the direct method. This suggests that the DNA polymorphism analysis can be utilized as an alternative method of the direct determination method or as a method for confirming the classification by the direct method.

(4) Classification of Varieties Based on the Thermostability by Each Method.

The classification of varieties by each method is shown in Table 1. Types A and C classified by the direct method correspond to Sd2 classified by the isoelectric point. As to type B, a variety with a relatively higher thermostability corresponds to Sd2, and a variety with a lower thermostability corresponds to Sd1. Therefore, the type B is further divided into type B1 and type B2, so that the varieties are finally classified into four types.

Barley varieties of type A are observed in Japanese varieties, many varieties of type B are observed in Canada, the United States and Europe, and many of type C are observed in varieties induced in the breeding process of Japanese barley as well as in old type of varieties and Australian varieties.

2. A Method for Identifying a Variety Having Beer Brewing Property Based on the Thermostability of β-amylase One beer brewing property, fermentability, can be defined by the apparent attenuation limit or final attenuation. The final attenuation can be expressed as a percentage of the amount of extract consumed by fermentation versus the amount of extract in the wort before fermentation when wort is fermented up to the peak level by yeast. To determine of the fermentability, fresh operating yeast (0.5–4 g) may be added to 200 ml of the wort which contains a known amount of extract and fermented at 25–30° C. (3–5 days). After fermentation, yeast cells are separated, the extract in a fermentation solution is quantified. The apparent extract is an amount of extract determined in a fermentation solution in its entirety without removing alcohol from the fermentation solution. The real extract is an amount of extract determined in a solution where a certain amount of a fermentation solution is taken and alcohol is evaporated and subsequently water is added to back to the initial weight. The fermentability calculated using an apparent extract is referred to as "apparent attenuation limit", and the fermentability calculated using a real extract is referred to as "final attenuation".

As described above, the degree of the apparent attenuation limit is preferred in order to determine fermentability which is one of malting barley brewing property.

The relationship between the classification of varieties based on the β-amylase described above and the apparent attenuation limit was also investigated. The result revealed that there is a relationship between the thermostability of β-amylase and the character of barley. That is, a variety with a higher thermostability of β-amylase indicates higher apparent attenuation limit (FIG. 1).

A variety with high thermostability is a variety having 20% or more, preferably 30% or more, more preferably 40% or more, of the relative remaining activity by the above direct determination method. Therefore, at least type A varieties have a preferable brewing character among the class of varieties based on the thermostability of the above β-amylase.

According to this, a variety having a good brewing character can be identified as a variety with high apparent attenuation limit (for example, type A), using any of the above determination methods, an equivalent method, or their combination.

As described above, it is possible to identify a variety and to simply identify barley having a good brewing property by determining the thermostability of barley βamylase using the above convenient determination method in the early breeding. As a result, it is possible to identify barley having a good brewing property in the early stage, and to significantly reduce the period of breeding, save labor, reduce costs, and to select with certainty barley of interest for brewing purposes.

To more conveniently conduct the above method for identifying a variety and the breeding method, materials required for these methods can be provided as a kit. The kit may include, for example, reagents required for each determination method, a reference sample, and instructions which describe a determination method.

The invention will now be explained in detail by the following experimental examples, though the invention is not in any way limited to these examples.

EXAMPLES

Example 1

Extraction of Crude Enzyme Solution

One fully ripe barley seed was ground in 1 ml of 50 mM acetate buffer (pH 5.5) containing 10 mM DTT (dithiothreitol), and then incubated overnight at 4° C. Subsequently, the solution was centrifuged at 15,000 rpm for 10 minutes to obtain the supernatant in the form of a crude enzyme solution.

Example 2

Examination of Differences Among Varieties Using the Thermostability of β-amylase The crude enzyme solution was diluted with 50 mM Good buffer (Wako Pure Chemicals Co. Ltd.) containing 1% bovine serum albumin by 100 folds, and 30 μl of the diluted crude enzyme solution was heat treated at 57.5° C. for 30 minutes. Subsequently, the activity of β-amylase of both heat treated samples and non-heat treated samples was determined by using β-amylase activity determination kit "DIACOLOR-AMY" (Ono Pharmaceutical Co. Ltd.). The relative remaining activity after heating of each variety was shown by standardization as the rate of activity of heat treated samples when the activity of the non-heat treated samples is defined as 100% (Table 1). This relative remaining activity was divided into three main types: a variety which indicated about 40–60% as relative remaining activity (type A thermostability), a variety which indicated about 10–30% (type B thermostability), and a variety which lost most enzyme activity (type C thermostability) (Table 1).

Example 3

Examination of Differences Among Varieties Using the Isoelectric Point of β-amylase The isoelectric focusing electrophoresis of 1 μl of the above crude enzyme solution was conducted using FAST SYSTEM (Pharmacia). The gel for electrophoresis was FAST GEL IEF4–6.5 (Pharmacia). After electrophoresis, the gel was sank in 20 mM Tris-HC1 buffer (pH 7.5) containing 3% soluble starch, and was stained with an iodine solution (0.02% I2, 0.2544% KI). As a result of this, the pattern of the isoelectric focusing electrophoresis of the examined varieties was classified into two types: one with a band of pI 6.5 (Sd1), and the other without a band of pI 6-5 (Sd2). Examination of the relation between the electric point and thermostability of β-amylase revealed that Sd2 was observed in all types A, B, and C, while Sd1 was observed in only type B (Table 1). According to this result, type B of thermostability was further divided into type B1 and B2 by types of the isoelectric points.

TABLE 1

Thermostability type and isoelectric focusing pattern of β-amylase.

| Varieties | Relative remaining activity (%) | Type of Thermo-stability | Pattern of isoelectric point |
|---|---|---|---|
| Satsukibare | 53.1 | A | |
| Seijo 15 | 52.9 | A | |
| Amagi Nijo | 52.8 | A | Sd2 |
| Kanto Nakate Gold | 52.4 | A | |
| Svanhals | 52.0 | A | |
| Golden Melon | 51.5 | A | Sd2 |
| Tone Nijo | 51.3 | A | |
| Mikamo Golden | 51.2 | A | |
| K3 | 51.1 | A | |
| Akagi Nijo | 50.9 | A | |
| G65 | 50.8 | A | |
| Ko 1–18 | 50.7 | A | |
| Tsuyushirazu | 50.6 | A | |
| Karl | 50.4 | A | Sd2 |
| Hatukaze | 50.4 | A | |
| Nittakei 1 | 50.4 | A | |
| Ebisu | 50.3 | A | |
| Kaneko Gold | 50.1 | A | |
| Aichi Wase 13 | 50.1 | A | |
| Seijo 17 | 49.1 | A | |
| Haruna Nijo | 49.1 | A | Sd2 |
| New Golden | 48.7 | A | |
| Ko A | 48.4 | A | |
| Mokusekikou 3 | 48.3 | A | |
| Cambrinus | 47.7 | A | |
| Ko 3–6 | 47.5 | A | |
| Kirin Choku 1 | 47.2 | A | |
| Nishino Gold | 46.6 | A | |
| Misato Golden | 46.5 | A | |
| Myogi Nijo | 44.4 | A | Sd2 |

TABLE 1-continued

Thermostability type and isoelectric focusing pattern of β-amylase.

| Varieties | Relative remaining activity (%) | Type of Thermo-stability | Pattern of isoelectric point |
|---|---|---|---|
| Sapporo 7 | 43.9 | A | |
| Ryofu | 43.0 | A | |
| Hoshimasari | 41.1 | A | |
| Robust | 23.0 | B | Sd2 |
| Azure | 22.3 | B | Sd2 |
| Igri | 19.9 | B | Sd2 |
| Manker | 19.2 | B | Sd2 |
| Koujitu 1 | 16.5 | B | Sd2 |
| Alexis | 16.0 | B | Sd1 |
| Bonanza | 16.0 | B | Sd1 |
| Manley | 14.9 | B | Sd1 |
| Klages | 14.6 | B | Sd1 |
| Morex | 12.7 | B | Sd1 |
| Harrington | 12.7 | B | Sd1 |
| Triumph | 10.0 | B | Sd1 |
| Franklin | 9.7 | B | Sd1 |
| Union | 3.0 | C | |
| Seijo 511 | 3.0 | C | |
| Nirasaki Wase 1 | 2.8 | C | Sd2 |
| Golden Promise | 2.5 | C | Sd2 |
| Fuji 2 | 2.4 | C | |
| Chevallier | 2.4 | C | |
| Hakata 2 | 2.1 | C | Sd2 |
| Beacon | 1.8 | C | Sd2 |
| Sewa | 1.6 | C | |
| Asahi 5 | 1.5 | C | |
| Asahi 19 | 1.4 | C | |
| Azuma Golden | 1.2 | C | |
| Duckbill | 1.2 | C | |
| Schooner | 1.1 | C | |
| Clipper | 1.0 | C | |
| Dampier | 0.8 | C | |
| Beka | 0.8 | C | |
| Stirling | 0.7 | C | |
| Proctor | 0.7 | C | |
| Hiproly | 0.4 | C | |
| Prior | 0.4 | C | |

Example 4

Examination of DNA Polymorphisms Using Molecular Selection Technique 4-1) Isolation of DNA:

One g of green barley leaf at seedling stage was ground in a mortar together with liquid nitrogen, and suspended to 1 ml of 2x CTAB solution. 1x CTAB solution was added to this suspension to adjust to 4 ml of volume, and then shaken at 60° C. for 30 minutes. After shaking, 2 ml of chloroform-isoamyl alcohol solution (24:1) was added to the suspension, which was then shaken at room temperature. The lower layer was then removed. This protein removal operation was repeated twice. To the collected upper layer, ¹⁄₁₀ volume of 10% CTAB solution and ⅔ volume of CTAB precipitating solution were added and allowed to stand overnight to precipitate nucleic acid. This solution was centrifuged, and was suspended to 1 ml of 1 M NaCl-TE solution, and RNase was added to this suspension to digest RNA. After this treatment, 2 ml of 2-propanol was added to precipitate DNA and washed with 70% ethanol three times, and finally was suspended to 100 μl of sterilized water to obtain DNA sample.

4-2) RFLP Analysis:

5 μl of the entire barley DNA was digested with XbaI, and subsequently agarose electrophoresis was conducted. After electrophoresis, DNA was transferred to a Boehringer positive nylon membrane under alkaline denature, and Southern blotting was conducted using this transferred membrane. A probe was created using the β-amylase structural gene of Haruna Nijo seed as a template. The temperature condition of hybridization was set to 42° C. After hybridization, the membrane was washed. In washing, 15 minutes of washing step at 56° C. was conducted twice using 2_SSC-1% SDS solution, and then 15 minutes of washing step at 56° C. was conducted twice using 0.1_SSC-1% SDS solution. After washing, the detection of probe was conducted by the DIG method. As a result of this, Haruna Nijo (type A of thermostability), Bonanza (type B), and Schooner (type C) indicated 3.1 kbp, 4.1 kbp, and 2.7 kbp of positive bands respectively. Further, their mated progeny lines also indicated the same bands, with hetero type having two bands of both parents.

4-3) CAPS Analysis:

PCR was conducted using the entire barley DNA isolated by the CTAB method as a template, and the following primer used were as follows:
5' end primer: 5'-TGGTAGAGGCCGCTGT-GGATGGTGTCATGG-3' (SEQ ID NO: 1), and 3' end primer: 5'-CCGCCGCTGCTGCTGCTTTGAA-3' (SEQ ID NO: 2).

It has been confirmed that these primers can amplify 1.7 kbp of upstream of the β- amylase structural gene of Haruna Nijo.

PCR was conducted under the following conditions: the denaturing step at 94° C. for one minute, the annealing step at 55° C. for 2 minutes, and the extending step at 72° C. for 6 minutes. This cycle was repeated 25 times, and, after the final cycle, the extending step was conducted at 72° C. for 6 minutes.

The PCR product was digested with Bgl II, and subsequently the electrophoresis was conducted. As a result of this, Haruna Nijo with type A of thermostability indicated a band of 1.1 Kb, while Harrington with type B, and Schooner with type C were not digested with Bgl II, indicating a band of 1.7 Kb. In their mated progeny lines, this CAPS form correspond to the above RFLP form.

From the result of 4-2) and 4-3), the thermostability of the β-amylase completely corresponded to DNA polymorphisms of the structural region, showing that selection can be conducted by the method.

Example 5

Relation Between Thermostability of β-amylase and Brewing Property

To investigate the relationship between the type of thermostability of β-amylase and beer brewing property, the relative remaining activity (%) of β-amylase when the enzyme was treated with heat at 57.5° C. and data concerning barley brewing properties was plotted. Their correlation was then examined (FIG. 1). As a result of this, in variety populations of breeding lineage consisting of population with type A and C, type A tends to indicate higher degree of apparent attenuation limit as compared to type C. This result shows that the thermostability of β-amylase significantly influence the degree of the apparent attenuation limit.

Furthermore, to evaluate whether thermostability of β-amylase is effective as an indicator for indirect selection of beer brewing property, the thermostability of β-amylase and the degree of the apparent attenuation limit of progeny lines of crossing of types A and B (F7 or more) was investigated and compared. In the investigated progeny lines, the thermostability separated into types A and B, while in a progeny lines where both parents are the same, lines of type A indicated higher degree of apparent attenuation limit than type B (FIG. 2). In barley breeding, it is common practice to select a good variety from various progeny lines whose parents are the same. Therefore, this result has shown that it is possible to select and breed a line which indicates a high degree of apparent attenuation limit using the type of thermostability as an indicator.

From the above results, it is possible to control and improve quality of brewing products by applying a barley variety with a preferable brewing character which is selected and bred herein.

It is possible to use the above method for determining the thermostability of β-amylase alone, but it is desirable to combine the above methods in order to obtain certain results. Further, it is possible to select and use the suitable method depending on various situation of breeding process.

As described above, the present invention makes it possible to identify each thermostable variety, using the thermostability of β-amylase, which the variety possesses, as an indicator. Since this β-amylase is very important enzyme specifically for breeding, it is possible to control and improve quality of the product through identifying and selecting a barley variety which becomes materials of the brewing product by the method for identifying a variety.

This method for identifying a variety which has higher apparent attenuation limit can be conducted toward the brewing property of interest in any stage of breeding process. Particularly, the possibility that barley having a good brewing property selected with certainly in the early breeding makes it possible to shorten the time period of breeding and reduce the breeding scale. In addition to reducing of the period of breeding and the breeding scale, a reduction of the cost required for breeding and remarkable labor-saving can also be accomplished, because the selection can be done by a more convenient method as compared to the conventional barley analysis.

Furthermore, since it is possible to examine whether or not a variety has a brewing property of interest in any stage of the breeding process, the breeding goals can be achieved. Particularly, it is possible to know with certainty the homogenesis of the gene of the interest in the breeding process especially by measuring DNA polymorphisms. As a result of this, it is unnecessary to investigate the character in the breeding process since homogenesis.

Further, since the inventive method for identifying a variety, unlike the conventional method, is not in any way affected by environmental or climatic conditions, highly reliable evaluation associated with the existence of the brewing property of the interest can be achieved.

Furthermore, the present invention is remarkably effective for cultivating a variety using the method for producing an isogeneic line in order to improve the degree of apparent attenuation limit. Using the present invention, a variety can be produced easily merely by repeating mating and selecting the individual having the breeding property of the interest using the DNA polymorphism analysis.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Hei 9-170,582, filed Jun. 26, 1997, and incorporated herein by reference in its entirety.

What is claimed is:

1. A method for selecting a barley variety with improved fermentability for brewing from a population of breeding lineages consisting of Types A, B and C, based on the thermostability of a β-amylase encoded by the barley, which comprises:

(a) heating a solution of said β-amylase, expressed by the barley variety, at 57.5° C. for 30 minutes, and measuring the thermostability therefrom with a relative remaining activity after heating as an indicator of said thermostability;

(b) classifying the barley variety into one of the following three types:
  (i) Type A, wherein 40% or more relative activity is retained after said heating;
  (ii) Type B, wherein 10–30% relative activity is retained after said heating; and
  (iii) Type C, wherein 3% or less relative activity is retained after said heating; and (c) selecting Type A from the population of breeding lineages consisting of populations of Types A and B; or selecting Type A from the population of breeding lineages consisting of Types A and C; or selecting Type B from the population of breeding lineages consisting of Types B and C; or selecting Type A from the population of breeding lineages consisting of Types A, B, and C, whereby the selected barley variety displays improved fermentability.

2. The method of claim 1, wherein the barley variety selected retains at least 40% of the relative activity after said heating.

3. The method of claim 1, wherein the solution of β-amylase is a solution extracted from barley seeds.

4. The method of claim 1, wherein the barley variety selected retains from 41.1 to 53.1% relative remaining activity after said heating.

5. A method for selecting a barley variety for brewing from a population of breeding lineages consisting of Types A, B and C, based on the thermostability of a β-amylase encoded by the barley, which comprises:

a) classifying the barley variety into one of the following three types
  A) Type A corresponds to 40% or more relative activity being retained after heating a solution of said β-amylase variety at 57.5° C. for 30 minutes;
  B) Type B corresponds to 10–30% relative activity being retained after heating a solution of said β-amylase variety at 57.5° C. for 30 minutes, said Type B having a higher thermostability component, B1, corresponding to Sd2, and a lower thermostability component, B2, corresponding to Sd1; and
  C) Type C, wherein 3% or less relative activity is retained after heating a solution of said β-amylase variety at 57.5° C. for 30 minutes;

b) measuring an isoelectric point (pI) of a solution of said β-amylase, and determining whether the β-amylase has a pI band of about 6.5; and c) classifying the barley variety into one of two types:
  (i) Sd1, having a pI band at about 6.5; and
  (ii) Sd2, not having a pI band at about 6.5;

wherein each of Types A and C exhibit Sd2 pattern, and Type B exhibits Sd1 or Sd2 patterns, and d) selecting Type A (Sd2) from the population of breeding lineages consisting of Type A (Sd2) and B (Sd1), or selecting Type B (Sd1) from the population of breeding lineages consisting of Type B (Sd1) and Type B (Sd2), or selecting Type B (Sd1) from the population of breeding lineages consisting of Type B (Sd2) and Type C (Sd2).

6. A method for selecting a barley variety which exhibits an apparent attenuation limit indicating improved fermentability, which comprises:

a) detecting polymorphisms of a gene encoding the β-amylase, and determining whether the polymorphisms have a recognition site for restriction enzyme Bgl II in the β-amylase gene region between SEQ ID NO:1 and the complementary site of SEQ ID NO:2; and b) selecting the barley variety which contains said recognition site, which corresponds with a Type A barley variety, wherein 40% or more relative activity is retained after heating a solution of said β-amylase at 57.5° C. for 30 minutes.

7. A method of breeding a barley variety which exhibits an apparent attenuation limit indicating improved fermentability, which comprises:

a) selecting a barley variety in accordance with claim 1, which encodes for a thermostable β-amylase; and b) breeding said variety for use in brewing.

8. A method of breeding a barley variety which exhibits an apparent attenuation limit indicating improved fermentability, which comprises:

a) selecting a barley variety in accordance with claim 5, which encodes for a thermostable β-amylase; and b) breeding said variety for use in brewing.

9. A method of breeding a barley variety which exhibits an apparent attenuation limit indicating improved fermentability, which comprises:

a) selecting a barley variety in accordance with claim 6, which encodes for a thermostable β-amylase; and b) breeding said variety for use in brewing.

* * * * *

UNITED STATES PATENT AND TRADEMARK OFFICE
CERTIFICATE OF CORRECTION

PATENT NO. : 6,492,576 B2  
DATED : December 10, 2002  
INVENTOR(S) : Kihara et al.

It is certified that error appears in the above-identified patent and that said Letters Patent is hereby corrected as shown below:

<u>Title page,</u>
Item [45] and the Notice information should read as follows:

-- [45] **Date of Patent: \*Dec. 10, 2002**

[\*] Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days. --

Signed and Sealed this

Twenty-ninth Day of April, 2003

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
tggtagaggc cgctgtggat ggtgtcatgg                                  30

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
ccgccgctgc tgctgctttg aa                                          22